United States Patent [19]
Ladewski

[11] Patent Number: 6,100,990
[45] Date of Patent: Aug. 8, 2000

[54] METHOD AND APPARATUS FOR DETERMINING REFLECTIVE OPTICAL QUALITY USING GRAY-SCALE PATTERNS

[75] Inventor: Theodore B. Ladewski, Ann Arbor, Mich.

[73] Assignee: Ford Motor Company, Dearborn, Mich.

[21] Appl. No.: 09/332,234

[22] Filed: Jun. 14, 1999

[51] Int. Cl.⁷ .................................................. G01N 21/55
[52] U.S. Cl. ............................................ 356/445; 356/124
[58] Field of Search ............................... 356/445, 237.2, 356/124–127

[56] References Cited

U.S. PATENT DOCUMENTS

| | | |
|---|---|---|
| 4,076,426 | 2/1978 | Gross et al. . |
| 4,255,055 | 3/1981 | Schave . |
| 4,285,745 | 8/1981 | Farabaugh . |
| 4,291,990 | 9/1981 | Takasu . |
| 4,461,570 | 7/1984 | Task et al. . |
| 4,647,197 | 3/1987 | Kitaya et al. . |
| 4,742,237 | 5/1988 | Ozawa . |
| 4,776,692 | 10/1988 | Kalawsky . |
| 4,802,759 | 2/1989 | Matsumoto et al. . |
| 4,866,287 | 9/1989 | Weber . |
| 4,895,448 | 1/1990 | Laird . |
| 5,003,187 | 3/1991 | Zumbrunn et al. . |
| 5,076,698 | 12/1991 | Smith et al. . |
| 5,128,550 | 7/1992 | Erbeck . |
| 5,135,308 | 8/1992 | Kuchel . |
| 5,135,309 | 8/1992 | Kuchel et al. . |
| 5,146,293 | 9/1992 | Mercer et al. . |
| 5,175,601 | 12/1992 | Fitts . |
| 5,225,890 | 7/1993 | Lee et al. . |
| 5,307,151 | 4/1994 | Hof et al. . |
| 5,309,222 | 5/1994 | Kamei et al. . |
| 5,311,286 | 5/1994 | Pike . |
| 5,315,384 | 5/1994 | Heffington et al. .................. 348/93 |
| 5,319,445 | 6/1994 | Fitts . |
| 5,343,288 | 8/1994 | Cohen et al. . |
| 5,343,294 | 8/1994 | Kuchel et al. ........................ 356/376 |
| 5,367,378 | 11/1994 | Harding et al. . |
| 5,452,079 | 9/1995 | Okugawa . |
| 5,471,297 | 11/1995 | Tani . |
| 5,471,307 | 11/1995 | Koliopoulos et al. . |
| 5,568,258 | 10/1996 | Uemura et al. ....................... 356/371 |
| 5,581,352 | 12/1996 | Zeien . |
| 5,581,356 | 12/1996 | Zeien ................................. 356/376 |
| 5,612,786 | 3/1997 | Huber et al. . |
| 5,636,025 | 6/1997 | Bieman et al. . |
| 5,646,733 | 7/1997 | Bieman . |
| 5,691,784 | 11/1997 | Hausler et al. . |
| 5,691,811 | 11/1997 | Kihira . |
| 5,694,479 | 12/1997 | Guering et al. . |

FOREIGN PATENT DOCUMENTS

| | | |
|---|---|---|
| 0 769 674 A2 | 4/1997 | European Pat. Off. . |
| 44 15 834 A1 | 11/1995 | Germany . |
| 8-328150 | of 1996 | Japan . |
| WO 96/12160 | 4/1996 | WIPO . |

OTHER PUBLICATIONS

Takeda et al., Fourier–transform method of fringe–pattern analysis for computer–based topography and interferometry, vol. 72, No. 1, Jan. 1982, pp. 156–160.

(List continued on next page.)

*Primary Examiner*—Robert H. Kim
*Assistant Examiner*—Phi Natividad
*Attorney, Agent, or Firm*—Jerome R. Drouillard; Roger L. May

[57] ABSTRACT

A method of determining reflective optical quality of a reflective product includes reflecting a first gray-scale pattern off the product; obtaining a first image of the first pattern with an image pickup device after the first pattern has reflected off of the product; and determining optical quality of the product based on data obtained from the first image. An apparatus for determining reflective optical quality of such a product is also disclosed.

16 Claims, 5 Drawing Sheets

OTHER PUBLICATIONS

"Shearing Interferometer With Scanned Photodiode Array And Microcomputer For Automatic Transparency Distortion Measurements", by J. Taboada et al, SPIE vol. 153, Advances in Optical Metrology (1978), pp. 139–145.

"Interferometer For Measurement Of The Wedge And Lens Power Of Flat Glass And Laminates", by B.N. Dereck, Plastics Products Research, Parkersburg, WV, 5–2–78, pp. 1–7, plus attachments.

"Novel Three Dimensional Computer Vision Techniques With Applications To Deformation Measurement, 3–D Shape Gauging And Surface Quality Inspection", by Shouhong Tang, 1991, pp. 1–169.

"Laboratory Apparatus For The Optical Distortion Measurement In Automotive Windows", Budgetary Data Sheet, Two Sampesl of Computer Screen and Schematic Layout of Tai–Tecnologia Automazione Innovazione—S.p.A., 1994, Rome, Italy.

"A Human Factors Analysis Of Optical Distortion For Automotive Windshields", by Minoru Makiguchi et al, SAE Technical Paper No. 940390, dated Feb. 1994, pp. 47–57.

"A New Automatic Optical Distortion Measuring System For Automotive Windshields", by Shigeyuki Seto et al, SAE Technical Paper No. 940391, dated Feb. 1994, pp. 59–64.

"Novel Optical Techniques For Window Glass Inspection", by M. Savolainen et al, Meas. Sci. Technol. 6, ©1995 IPO Publishing Ltd., pp. 1016–1021.

"WaveScope—WaveScope™ wavefront Sensor Ssytem WFS–01, Table Top Optical Wavefront Sensor", Technical Bulletin of Adaptive Optics Associates, Inc., Cambridge, Massachusetts, 1997, 2 pp.

"Distortiometer Ssytem SD–1900—Digital Image Analysis System For Measuring Optical Distortion In Automotive Transparencies", Strainoptic Technologies Inc., North Wales, PA, Apr. 1997, 10 pp.

"Automatic On–Line Quality Control—Raw Glass Defects and Optical Quality Monitoring, FloatScan 'Cather' & 'Optics'", technical brochure of Grenzebach Corporation, Newnan, GA, Jul. 21, 1997, pp. 1–9.

"Inspection Of Float Glass Using A Novel Retro–Reflective Laser Scanning System", by Jonathan D. Holmes, Optical Scanning System: Design And Applications, SPIE vol. 3131, Jul. 30–31, 1997, San Diego, CA, pp. 180–190.

"Eliminating Optical Quality Headaches", Quality Control, Glass International, Sep. 1997, pp. 57, 59.

"LASOR" Technical Bulletin of Laser Sorter GmbH, Oct. 20, 1997, one page.

"Technical Support Package On Technique For Measuring Optical Quality of a Window", by David I. Brown et al, Feb. 1998, NASA Tech. Brief, vol. 22, No. 2, Item #109, 8 pp.

SAE Technical Bulletin No. 980917, "Measuring Curvature of Mirrors Using Image Analysis", by Dorothy J. Helder, Feb. 24, 1998, pp. 147–152.

"Holographic Optics And Machine Vision Inspection Systems For Flat Glass, Tubing & Pressed Ware", technical bulletin of TAI Incorporated, Chantilly, VA, undated, 4 pp.

"Ombroligne OM90", technical bulletin of Lasor Laser Sorter GmbH, Germany, undated, 1 pp.

"Windshield Optical Distortion Analyzer", technical brochure of R&D Reflections Inc. Wayne, Ohio, undated, 2 pp.

METHOD AND APPARATUS FOR DETERMINING REFLECTIVE OPTICAL QUALITY USING GRAY-SCALE PATTERNS

TECHNICAL FIELD

The invention relates to an apparatus and method for determining reflective optical quality of a reflective product using one or more gray-scale patterns, wherein the one or more patterns are reflected off of the product.

BACKGROUND OF THE INVENTION

A prior method for determining reflective optical quality of a reflective product, such as a front windshield for a motor vehicle, involves reflecting a point light source off of the product and onto a white screen. A camera is then used to measure intensity variations of the light as seen on the screen. This method, however, is subject to errors if reflective properties of the product are not uniform. For example, if the product has a surface coating with variations in thickness, such variations are interpreted as variations in optical power.

DISCLOSURE OF INVENTION

The invention overcomes the shortcomings of the prior art by providing a method and apparatus for determining reflective optical quality of a reflective product at any and all points on the product. Furthermore, the method and apparatus provide accurate and repeatable results.

Under the invention, a method of determining reflective optical quality of a reflective product includes reflecting a first gray-scale pattern off the product; obtaining a first image of the first pattern with an image pickup device after the first pattern has reflected off the product; and determining optical quality of the product based on data obtained from the first image.

Exemplary gray-scale patterns that may be used to practice the method include sinusoidal gratings as well as sawtooth gratings. Advantageously, the gray-scale patterns may be projected at the product, or generated on a reference place and reflected off of the product. Consequently, the method may be used with a variety of product and test configurations.

More specifically, the method includes determining a phase for each of a plurality of pixels of the first image, wherein each pixel corresponds to a particular point on the product. One or more optical characteristics are then determined for each of a plurality of points on the product based on the phase at the corresponding pixel.

An apparatus according to the invention for determining reflective optical quality of a reflective product includes an image generating device for generating a gray-scale pattern. The apparatus further includes an image pickup device for obtaining an image of the gray-scale pattern after the pattern has reflected off of the product, and an image analyzing device in communication with the image pickup device. The image analyzing device includes instructions for determining optical quality of the product based on the image of the gray-scale pattern.

These and other objects, features and advantages of the invention are readily apparent from the following detailed description of the best modes for carrying out the invention when taken in conjunction with the accompanying drawings.

BEST MODES FOE CARRYING OUT THE INVENTION

Figure 1:
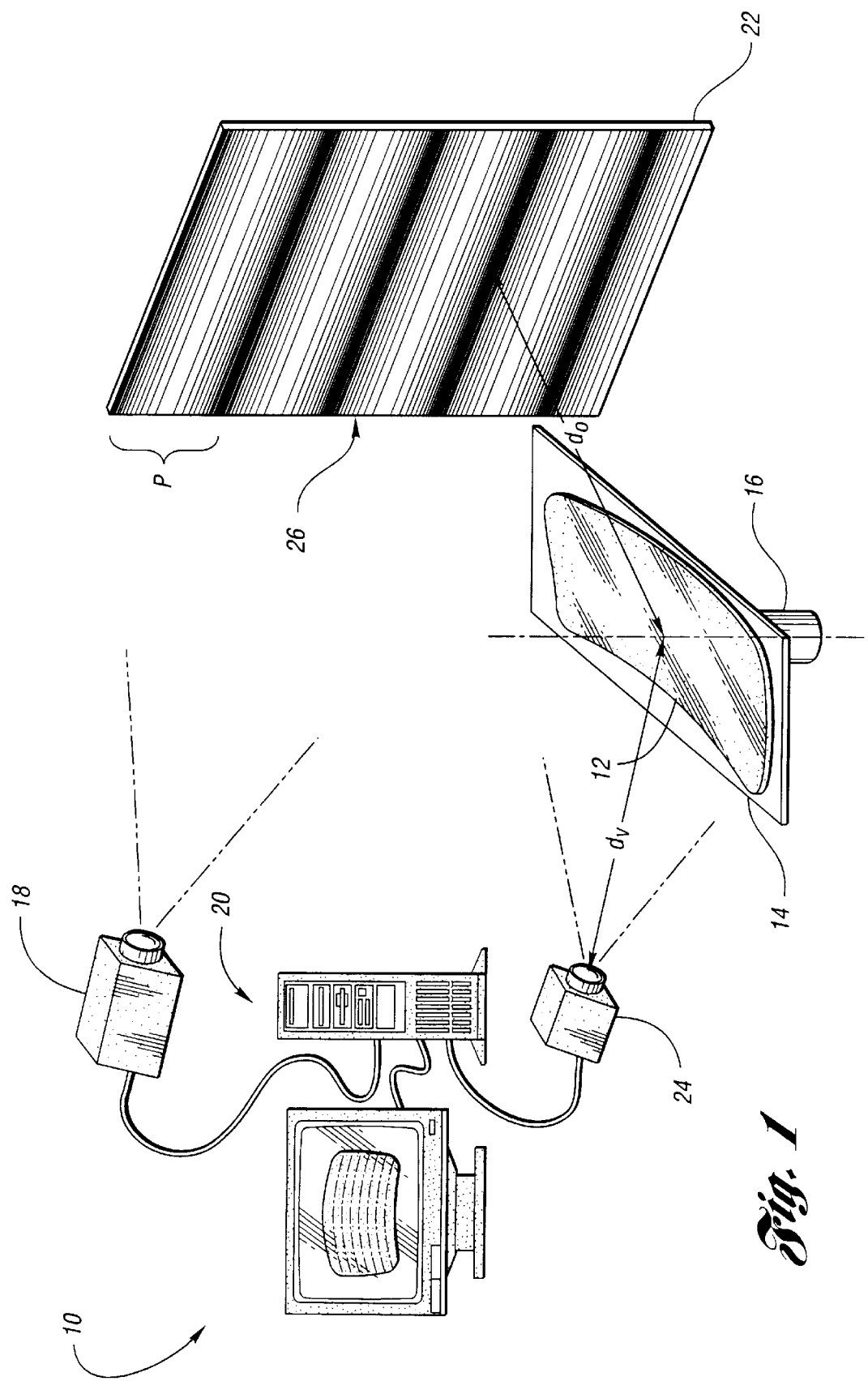
FIG. 1 is a schematic view of an apparatus for practicing a method according to the invention for determining reflective optical quality of a reflective product such as a motor vehicle windshield, wherein the apparatus includes a projector for projecting a sequence of phase-shifted sinusoidal gratings onto a screen, and a camera for obtaining images of the gratings as reflected off of the windshield.

FIG. 1 shows an apparatus 10 according to the invention for determining reflective optical quality of a reflective product, such as a front windshield 12 for a motor vehicle. Other exemplary reflective products include mirrors, windows and any other shiny, relatively smooth object. The windshield 12 is supported on a generally flat surface 14 of an optionally rotatable work table 16.

As shown in FIG. 1, the apparatus 10 includes a projector 18 in communication with a computer 20. The projector 18 is used to project one or more gray-scale targets or patterns onto a reference plane, such as a screen 22, which is located behind the windshield 12 at a distance do from the windshield 12. Gray-scale pattern as used herein refers to a pattern having a varying light intensity, such as sinusoidal grating or sawtooth grating, and the pattern has a well defined phase at each point that is coded by intensity. Advantageously, the projector 18 and computer 20 can be used to quickly generate and project a sequence of phase-shifted gray-scale patterns onto the screen 22. Alternatively, the apparatus 10 may include any suitable image generating device for providing one or more gray-scale patterns, such as a computer monitor, television monitor, painted pattern, or slide projector.

The apparatus 10 further includes an image pickup device, such as a digital camera 24, for obtaining digital images of the gray-scale patterns. Preferably, the camera 24 is disposed in front of the windshield 12 at a distance $d_v$ from the windshield 12, as shown in FIG. 1, so as to obtain digital images of the gray-scale patterns as reflected off of the windshield 12. The camera 24 is also in communication with the computer 20, and the camera 24 transmits signals to the computer 20 corresponding to the digital images. The computer 20 is used to process the signals so as to determine optical quality of the windshield 12 as explained below in greater detail.

A method according to the invention for determining reflective optical quality of the windshield 12 involves determining one or more optical parameters or characteristics of the windshield 12 at discrete locations or points on the windshield 12. The optical characteristics are determined based on phase changes introduced to one or more gray-scale patterns by the windshield 12, as a result of the patterns being reflected off of the windshield 12.

Optical characteristics that may be determined include instantaneous apparent magnification, focal length, optical power, and astigmatism. In order to calculate such characteristics, wrapped vertical and horizontal phase distributions of images of the one or more gray scale patterns are first determined. As used herein, vertical and horizontal phase distributions refer to vertical and horizontal phase values, respectively, at a plurality of pixels of the images. The phase distributions may be determined using any one of several known techniques.

If the windshield 12 is stationary, a phase-shift technique is preferably utilized. Under the phase-shift technique, in order to determine the vertical phase distribution introduced by the windshield 12, the projector 18 first projects a single reference point onto the screen 22 The camera 24 then obtains an image of the reference point as reflected off of the windshield 12, and transfers the image to the computer 20 where it is stored. Next, the projector 18 projects a horizontally oriented gray-scale pattern, such as a first grating 26 of horizontal lines having a sinusoidal intensity profile and a pitch p, onto the screen 22. The camera 24 then obtains an image of the first grating 26 as reflected off of the windshield 12, and the camera 24 transfers the image to the computer 20 where the image is stored. Alternately, the reference point may be incorporated into the first grating 26, and a single image of the reference point and the first grating 26 may be obtained.

Next, the projector 18, in cooperation with the computer 20, shifts the first grating 26 vertically by a distance p/n to create a second, phase-shifted grating (not shown), where n is the desired number of phase-shifted gratings to be utilized in determining the vertical phase distribution. Furthermore, should be greater than or equal to 3, and is preferably 4. The projector 18 then projects the second, phase-shifted grating onto the screen 22. Next, the camera 24 obtains an image of the second, phase-shifted grating, and transfers the image to the computer 20 where the image is stored.

This process is continued until n images have been obtained by the camera 24, and transferred to the computer 20. Thus, the phase-shift technique involves generating a sequence of n phase-shifted gray-scale patterns, and obtaining images of each pattern within the sequence as reflected off of the windshield 12. Furthermore, each image comprises a plurality of pixels, and each pixel corresponds to a particular point on the windshield 12.

Figure 2:
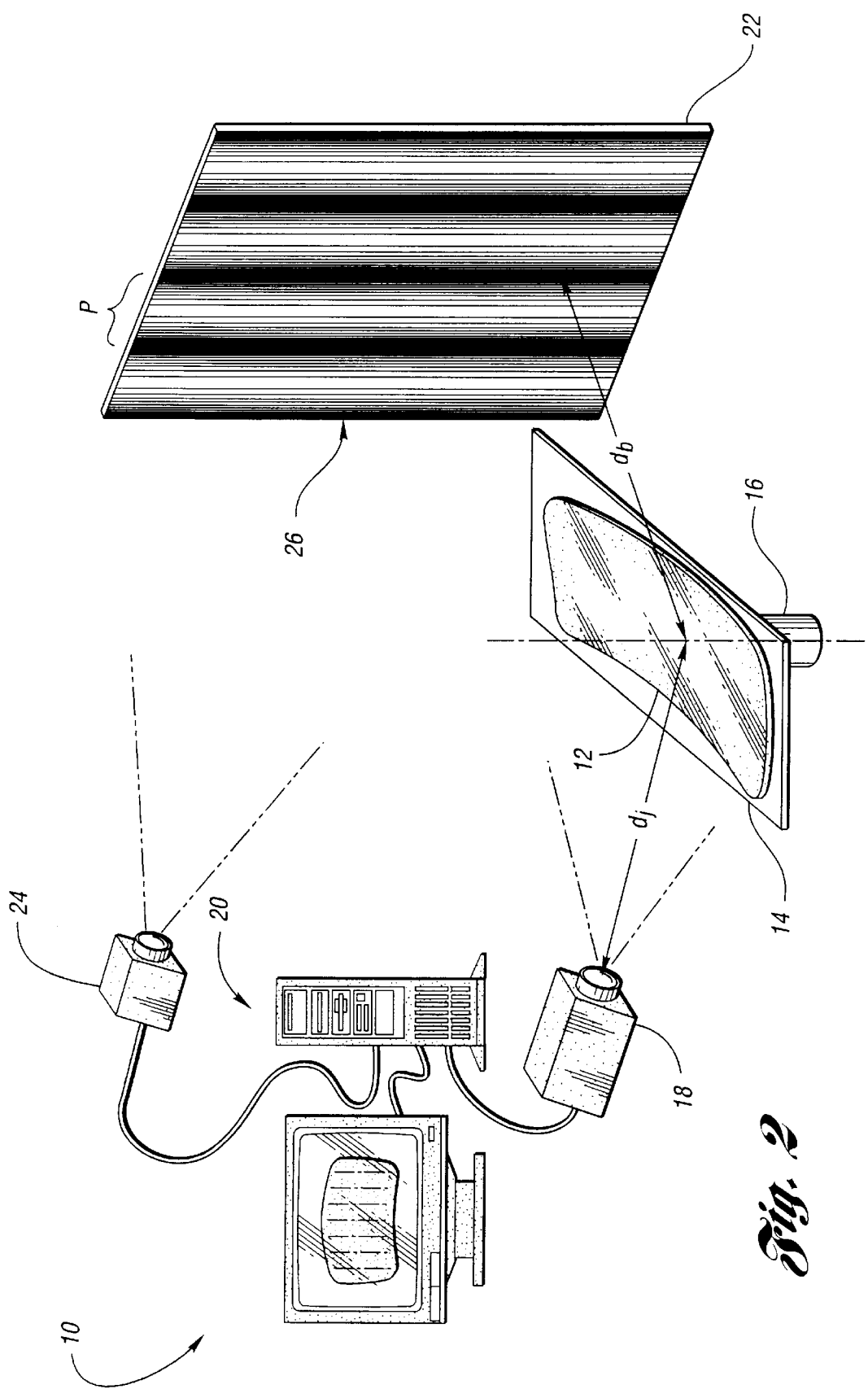
FIG. 2 is a schematic view of an alternative configuration of the apparatus, wherein the projector is positioned so as to project the sequence of phase-shifted sinusoidal gratings onto the windshield such that the gratings are reflected onto the screen, and the camera is positioned so as to obtain images of the gratings as seen on the screen.

Because this technique involves directing the camera 24 at the windshield 12 to obtain images of the patterns as reflected off of the windshield 12, it may be referred to as a view-at approach. Alternatively, as shown in FIG. 2, the phase-shift technique may involve projecting a sequence of phase-shifted gray-scale patterns at or onto the windshield 12 such that the patterns are reflected off of the windshield 12 and onto the screen 22 or other reference plane. This alternative approach further involves obtaining images of the patterns as seen on the screen 22. Such an approach may be referred to as a project-at approach. Generally, then, the method involves reflecting one or more gray-scale patterns off the windshield 12, wherein such a description covers both view-at and project-at approaches.

Next, the computer 20 analyzes the n images to determine vertical phase $\phi_y$ for each of the pixels of the images. The vertical phase $\phi_y$ for each pixel is determined based on light intensities at the same pixel location on the n different images, and the reference point is used to calibrate unwrapped vertical phase values. The general equation for determining $\phi_y$ for a particular pixel (x,y) is as follows:

$$\varphi(x, y) = \tan^{-1}\left[-\frac{\sum_{i=0}^{n-1} I_{i+1}(x, y)\sin\frac{2\pi i}{n}}{\sum_{i=0}^{n-1} I_{i+1}(x, y)\cos\frac{2\pi i}{n}}\right]$$

where $I_i(x,y)$=light intensity at pixel (x,y) of image i. For n=4, the equation becomes:

$\phi_y(x,y)$=arctan(($I_4(x,y)-I_2(x,y)$)/($I_1(x,y)-I_3(x,y)$)).

The above process is then repeated using the reference point and vertically oriented gray-scale patterns, such as a grating of vertical lines having a sinusoidal intensity and a known pitch, to determine horizontal phase $\phi_x$ for each of the pixels of the images.

If the windshield 12 is moving, then a Fourier transform technique is preferably utilized to determine the phase distributions. Under the Fourier transform technique, only one horizontally oriented gray-scale pattern and one vertically oriented gray-scale pattern are required to determine the vertical phase and horizontal phase, respectively, for each of the plurality of pixels. Briefly, this technique involves obtaining an image of each pattern, and performing a Fourier transform of each image. Next, each Fourier transform is edited, and an inverse Fourier transform is performed to determine the vertical and horizontal phases for each pixel. Additional details regarding the Fourier transform technique may be found in "Fourier-Transform Method of Fringe-Pattern Analysis for Computer-Based Topography and Interferometry," by M. Takeda, H. Ina, and S. Kobayashi, J. Opt. Soc. Am. 72, 156(1982), which is hereby incorporated by reference.

Figure 3:
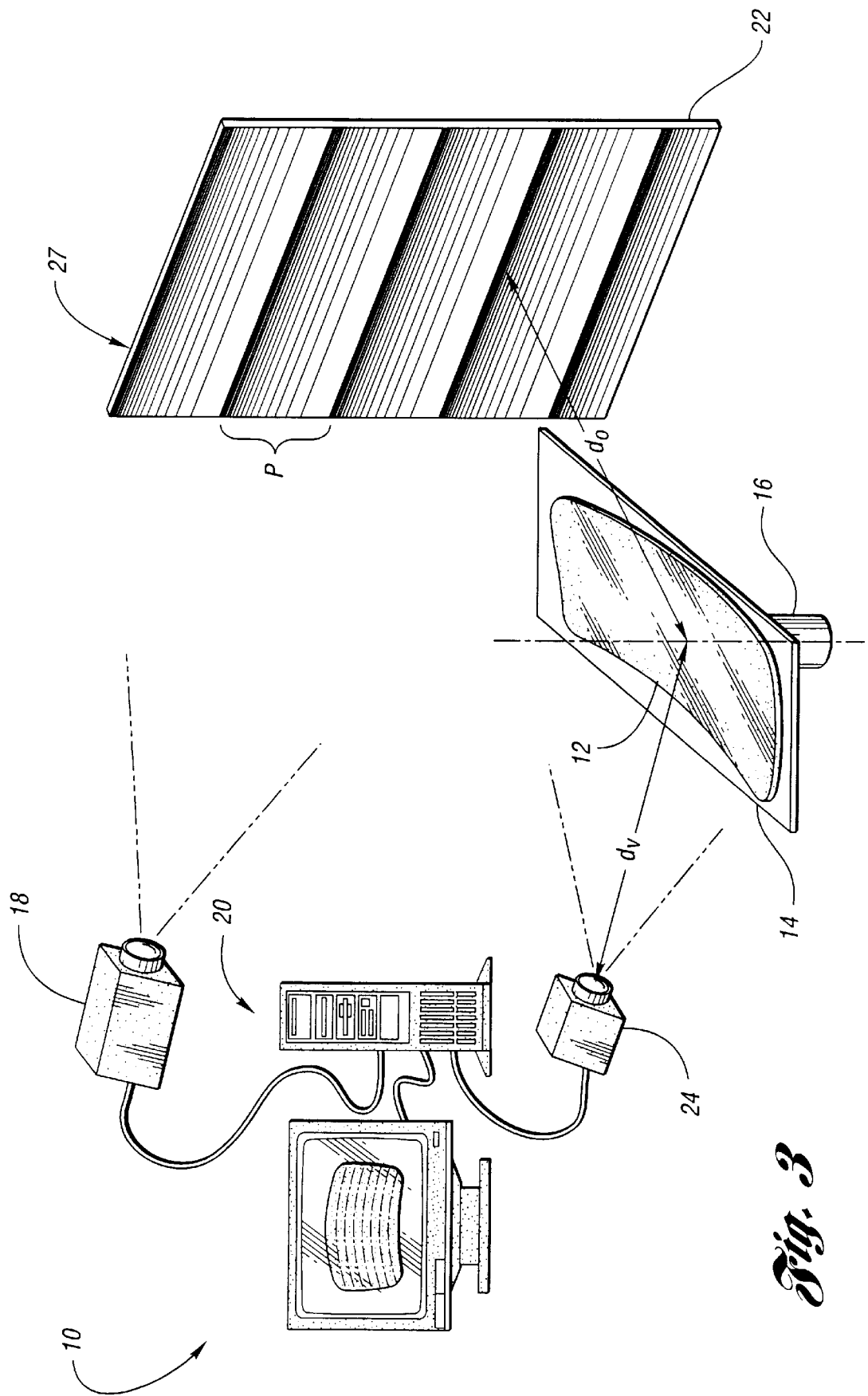
FIG. 3 is a schematic view of the apparatus having a similar configuration as in FIG. 1, and showing the projector projecting a sawtooth grating onto the screen.

If the camera 24 or other image pickup device has linear intensity response, and if the intensity profiles generated by the projector 18 or other image generating device are relatively accurate, then a technique that involves generating sawtooth gratings is preferably utilized to determine the phase distributions. Under this technique, as shown in FIG. 3, the projector 18 generates a horizontally oriented sawtooth grating 27 on the screen 22. The camera 24 then obtains an image of the sawtooth grating 27 as reflected off of the windshield 12, and the computer 20 acquires the image to determine a light intensity value I at each pixel (x,y).

Next, the projector 18 generates a uniformly white target on the screen 22, the camera 24 obtains an image of the white target as reflected off of the windshield 12, and the computer 20 acquires the image to determine a maximum light intensity value $I_{max}$ at each pixel (x,y). The projector 18 then generates a uniformly dark target on the screen 22, the camera 24 obtains an image of the dark target as reflected off of the windshield 12, and the computer 20 acquires the image to determine a minimum light intensity value $I_{min}$ at each pixel (x,y).

Next, the computer 20 determines the vertical phase $\phi_y$ at each pixel using the following equation:

$\phi_y(x,y)=2\pi(I(x,y)-I_{min}(x,y))/(I_{max}(x,y)-I_{min}(x,y))$

Similar to the phase-shift technique, the reference point is also used to calibrate unwrapped vertical phase values. Furthermore, a second phase-shifted and/or inverted horizontally oriented sawtooth grating may be required to fill in the phase distribution where the light intensity changes rapidly.

The above process is then repeated using the reference point and one or more vertically oriented sawtooth gratings to determine horizontal phase $\phi_x$ for each of the pixels of the corresponding images. Because this technique requires determination of only three variables for each pixel, phase distributions can be determined relatively quickly.

Alternatively, any other suitable technique for determining the phase distributions may be utilized, such as a phase synchronization technique, a demodulation-convolution technique, a 3-point Fourier fit, or a polynomial fit fringe order technique. Furthermore, any of the techniques may involve view-at or project-at approaches.

After the vertical and horizontal phase distributions have been determined, the computer 20 then determines the partial derivatives of the vertical and horizontal phases for each pixel point. The partial derivatives of the vertical phase for a particular pixel (x,y) may be determined using the following equations:

$$\frac{\partial \varphi_y}{\partial x}(x, y) = \varphi_y(x+1, y) - \varphi_y(x, y) + k\pi, \text{ and}$$

$$\frac{\partial \varphi_y}{\partial y}(x, y) = \varphi_y(x, y+1) - \varphi_y(x, y) + k\pi,$$

where k=−1, 0, or +1 as needed to correct for the 2π ambiguity in the wrapped phase. Similarly, the partial derivatives of the horizontal phase for a particular pixel (x,y) may be determined using the following equations:

$$\frac{\partial \varphi_x}{\partial x}(x, y) = \varphi_x(x+1, y) - \varphi_x(x, y) + k\pi, \text{ and}$$

$$\frac{\partial \varphi_x}{\partial y}(x, y) = \varphi_x(x, y+1) - \varphi_x(x, y) + k\pi.$$

Next, optical characteristics are determined for each point on the windshield 12 by determining optical characteristics at each corresponding pixel of the images based on the phase data obtained at each pixel. For example, instantaneous apparent vertical magnification $m_y$ and instantaneous apparent horizontal magnification $m_x$ may be determined at each pixel (x,y) using the following equations:

$$m_y(x, y) = \rho_y(x, y) \bigg/ \frac{\partial \varphi_y}{\partial y}(x, y), \text{ and}$$

$$m_x(x, y) = \rho_x(x, y) \bigg/ \frac{\partial \varphi_x}{\partial x}(x, y),$$

where $\rho_y$(x,y) and $\rho_x$(x,y) are the vertical reference phase gradient and horizontal reference phase gradient, respectively, at a particular pixel (x,y). As used herein, reference phase gradient at a pixel (x,y) refers to the rate of phase change at pixel (x,y) when apparent magnification is 1.0. In other words, reference phase gradient is the rate of phase change at a particular pixel of an undistorted image.

The derivation of the above equations regarding instantaneous apparent magnification will now be explained. Generally, apparent magnification $m_a$ for a typical mirror is defined as the ratio of the angle subtended by the image of an object, which is referred to as image angle, to the angle subtended by the object, which is referred to as object angle. For mirrors with varying apparent magnification values, instantaneous apparent magnification m in a direction $\omega_o$ is defined as the ratio of the change of image angle to object angle, and is represented by the following equation:

$$m(\omega_o) = \lim_{\Delta\omega \to 0} \Delta\omega_i / \Delta\omega_o = d\omega_i / d\omega_o,$$

where $\Delta\omega_i$ is the subtended image angle, and $\Delta\omega_o$ is the subtended object angle.

Figure 4:
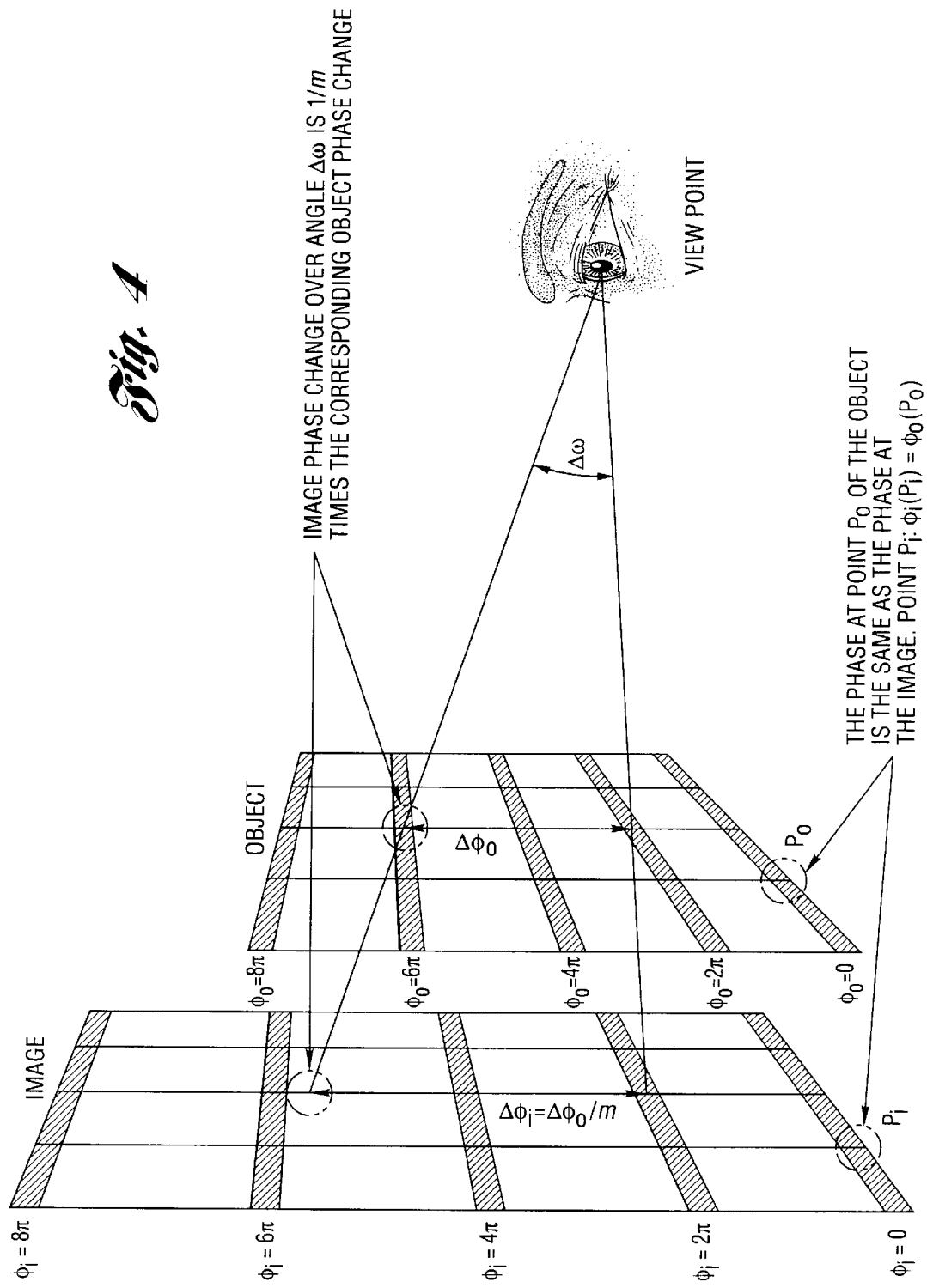
FIG. 4 is a schematic view of an object having a periodic structure, and an image of the object.

In the case where the object has a periodic structure, as shown in FIG. 4, such that each object point has a well defined phase, then each image point will have a phase identical with the phase at the corresponding object point. For example, the phase at a particular image point $P_i$ is identical to the phase at the corresponding object point $P_o$. Because $d\omega_i|dy_i = d\omega_o|dy_o$, the equation for m then becomes:

$$m = \frac{d\varphi_o}{dy_o} \bigg/ \frac{d\varphi_i}{dy_i}$$

where $\phi_o$ is the object phase and $\phi_i$ is the image phase.

For a particular image point (x,y), vertical and horizontal apparent magnifications $m_y$ (x,y) and $m_x$ (x,y), respectively, may be represented as:

$$m_y(x, y) = \frac{\rho_y(x, y)}{\frac{\partial \varphi_i}{\partial y_i}} \text{ and}$$

$$m_x(x, y) = \frac{\rho_x(x, y)}{\frac{\partial \varphi_i}{\partial y_i}}.$$

Thus, to determine magnification at a particular point on a mirror, the reference phase gradient is divided by the phase gradient as influenced by the mirror.

The reference phase gradients $\rho_y$ and $\rho_x$ may be determined using any suitable approach, such as a geometric approach. For simplicity, the discussion to follow will focus only on the relationship between the vertical reference phase gradient $\rho_y$ and the configuration of the apparatus 10. A similar approach may also be utilized to determine the horizontal reference phase gradient $\rho_x$.

Figure 5:
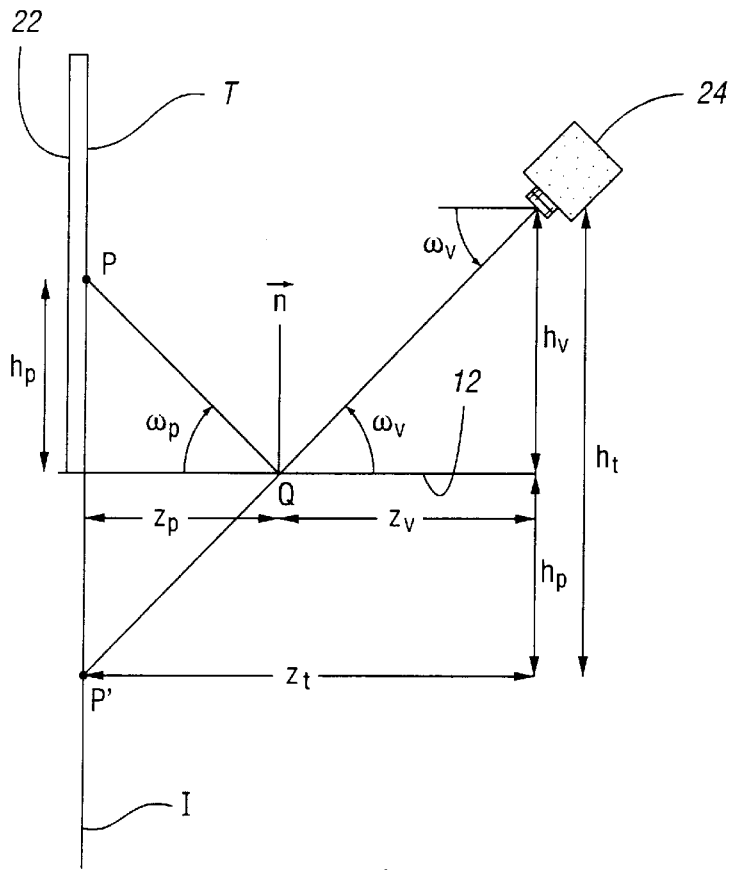
FIG. 5 is a schematic view of the windshield, the screen and the camera showing the geometrical relationship therebetween.

FIG. 5 shows the windshield 12 having a reference plane that is perpendicular to a target T, which is projected on screen 22. Target T comprises a gray-scale pattern having a varying light intensity profile and a pitch p. With this configuration, windshield 12 produces an image I of the target T. For example, when looking at a point Q on windshield 12, point P on target T can be seen as image point P'. Using the chain rule, the relationship between ρy, for a particular image pixel (x,y), and the configuration of the apparatus 10 can be written as $$\rho_y(x, y) = \frac{d\varphi_0}{dh_p} \frac{dh_p}{d\omega_v} \frac{d\omega_v}{dy},$$

where $\phi_0$(x,y) is the phase at pixel (x,y), $\omega_v$ is the angle of altitude and is optically equivalent to the previously described object angle $\omega_o$, $h_p$ is the height of target point P, which corresponds to pixel (x,y), $d\phi_0/dh_p$ equals 2π/p, and $d\omega_v/dy$ is a constant κ of the apparatus 10. The relationship can, therefore, be rewritten as:

$$\rho_y(x, y) = \frac{2\pi\kappa}{p} \frac{dh_p}{d\omega_v}.$$

In order to calculate the distance $h_p$, the wrapped vertical phase distribution must be unwrapped using one of several known algorithms to obtain the unwrapped vertical phase $\Phi_y$ at each pixel. The distance $h_p$ may then be determined by the following equation:

$$h_p = (\Phi_{yo}(x,y) - \Phi_0)p + h_{p0}$$

where $\Phi_{y0}$ is the unwrapped vertical phase at a reference pixel $(x,y_0)$, $\Phi_y(x,y)$ is the unwrapped vertical phase at pixel $(x,y)$, and $h_{p0}$ is a constant representing the height at point $(x,y_0)$.

Figure 6:
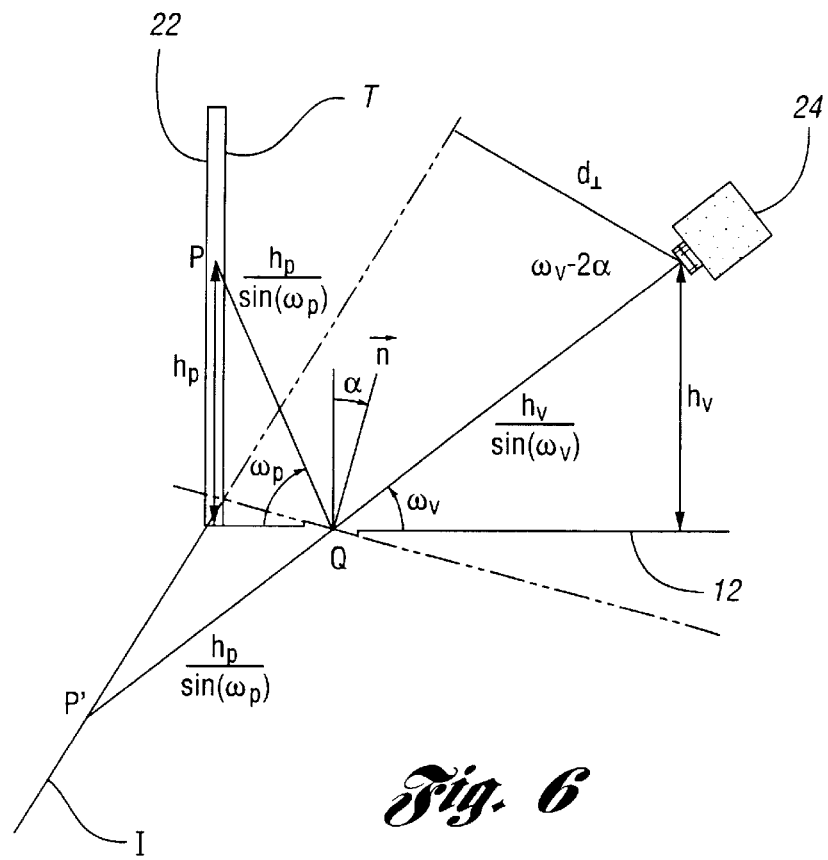
FIG. 6 is a schematic view of the windshield, the screen and the camera showing a surface facet of the windshield.

FIG. 6 shows that point Q may be located on a facet of the windshield 12, wherein the facet has a surface normal n at an angle α to the reference plane. Furthermore, the point Q is within a distance δ (not shown) of the reference plane, where δ is much less than vertical distance $h_v$ from the camera 24 to point Q. The error in calculating the reference phase gradient at point Q is approximately $\delta/z_v$. Given the above, $dh_p/d\omega_v$ may be expressed as follows:

$$\frac{dh_p}{d\omega_v} = \frac{d_\perp}{\cos^2(\omega_v - 2\alpha)},$$

The distance $d_\perp$ may be represented by the following equation:

$$d_\perp = [h_v/\sin(\omega_v) + h_p/\sin(\omega_p)]\cos(\omega_v - 2\alpha) = [h_v/\sin(\omega_v) + h_p/\sin(\omega_p)]\cos(\omega_p - \omega_v),$$

where $\omega_p = \arctan(h_p/z_p)$ and $\omega_v = \arctan(h_v/z_v)$. Distance $z_v$ (or alternately angle $\omega_v$) can be determined based on a standard camera calibration which relates coordinate location $(x,y)$ to $z_v$ through function $Z(xy)$. Distance $z_v$ can, therefore, be expressed as:

$$z_v = Z(x,y),$$

Distance $z_p$ may then be expressed as:

$$z_p = z_t - Z(x,y)$$

The reference phase gradients may also be measured using a procedure such as described below in detail. First, a test mirror that is optically flat is installed into a test arrangement. Next, a reference point $P_0$ is displayed on the screen 22, and $P_0$ is used to define unwrapped phase $\Phi_0$. The picture point $P_0'$ corresponding to point $P_0$ is then located. Next, the phase at $P_0'$ is determined by the following equation:

$$\frac{d\varphi_0}{dy}(x,y) = \varphi_0(x, y_0+1) - \varphi_0(x, y_0) + k\pi,$$

where k=1,0, or +1 as needed to correct for the 2π ambiguity in the wrapped phase. The reference phase gradient may then be determined from the following equation:

$$\rho_y(x,y) = \frac{d\varphi_0(x, y_0)}{dy}\left(\frac{\frac{dh_p(x,y)}{d\omega_v}}{\frac{dh_p(x,y_0)}{d\omega_v}}\right),$$

where $dh_p/d\omega_v$ may be determined as described above in detail.

Once instantaneous apparent magnification values have been determined at each pixel, additional optical characteristics of the windshield 12 may be determined. For example, optical power OP at each pixel may be determined in the x and y directions. Based on the thin lens formula and triangle relationships, the relationship between the instantaneous apparent magnification m and focal length f which is the reciprocal of OP, for a view-at approach is:

$$1/m = 1 - 1((1/d_o + 1/d_v)f),$$

where $d_o$ is the distance from the windshield 12 to the screen 22, and $d_v$ is the distance from the windshield 12 to the view point, such as the camera 24. For this equation to be valid, the focal length f must satisfy one of the two following conditions: either f<0, or f>1/(1/$d_o$+1/$d_v$). If f>1/(1/$d_o$+1/$d_v$), then the windshield 12 functions as a positive lens and forms a real image. In this case, the camera 24 must be between the windshield 12 and the real image.

Given the above expression for m, the vertical optical power $OP_y$ and the horizontal optical power $OP_x$ may be determined at each pixel (x,y) from the following equations:

$$OP_y(x,y) = 1/f_y(x,y) = (1/d_o + 1/d_v)(1 - 1/m_y(x,y)), \text{ and}$$

$$OP_x(x,y) = 1/f_x(x,y) = (1/d_o + 1/d_v)(1 - 1/m_x(x,y)),$$

where $m_y$ and $m_x$ are the instantaneous apparent magnifications in the vertical and horizontal directions, respectively. With these equations, $OP_y$ and $OP_x$ are determined based on the vertical position of the camera 24 relative to the windshield 12.

Because optical power of the windshield 12 is a function of the angle the windshield 12 is tipped toward or away from the camera 24 or view point, it is beneficial to determine optical power based on a standard view angle. Vertical optical power normal to a surface or facet of the windshield 12, $OPN_y$, may be determined at each pixel (x,y) from the following equation:

$$1/f_y(x,y) = (1/d_o + 1/d_v)(1 - 1/m_y(x,y))\cos(\omega_v - \alpha),$$

where $\omega_v$ is the angle of altitude, and α is the angle between a line normal to the particular surface or facet of the windshield 12 on which the corresponding material point (x,y) is disposed, and a line normal to a reference surface or plane of the windshield 12.

Additionally, vertical and horizontal focal lengths $f_y$ and $f_x$, respectively, may be determined at each pixel (x,y) by taking the reciprocals of the vertical and horizontal optical powers $OP_y$ and $OP_x$, respectively, at each pixel (x,y).

For a project-at approach, the relationship between the instantaneous apparent magnification m and the focal length f is:

$$m = [(d_j + d_b)f - d_j d_b]/(d_j f),$$

where $d_j$ is the distance from the windshield 12 to the projector 18, and $d_b$ is the distance from the windshield 12 to the screen 22. Focal lengths and optical powers in the x and y directions may then be determined for each pixel using this relationship.

In order to evaluate optical distortion perceived by a human observer, it is helpful to have an optical measure that accounts for the distance the observer will be from the windshield 12 during use. One such optical measure is standardized apparent magnification $m_s$ which may be used to evaluate optical effects as perceived by the occupant when looking at an object at infinity while located a standard distance $d_s$ from the windshield 12. Using the above equations involving instantaneous apparent magnification m and focal length f, the standardized apparent magnification $m_s$ may be expressed as:

$$m_s = \left(1 - \frac{1}{(1/d_s + 1/\infty)f}\right)^{-1} = (1 - (d_s/d_o + d_s/d_v)(1 - 1/m))^{-1},$$

where m and f are determined in the x or y directions, as necessary, using the procedure described above in detail. With this equation, standardized apparent magnification $m_s$ may be determined in the x and y directions at each pixel.

Another aspect of the invention involves evaluating astigmatic characteristics of the windshield 12. If the instantaneous apparent magnification m for a particular point (x,y) is not the same in all directions, then the windshield 12 is astigmatic at point (x,y). In such a case, point (x,y) will have a maximum instantaneous apparent magnification a in a certain direction θ, and a minimum instantaneous apparent magnification b in a direction perpendicular to θ, where θ is referred to as cylinder axis angle.

Discrete phase differences may be used to determine maximum and minimum instantaneous apparent magnifications a and b, as well as cylinder angle θ for each point on the windshield 12. The discrete phase differences are expressed by the following equations:

$$\Delta_y\phi_y = \phi_y(x,y+1) - \phi_y(x,y) = [(ac^2 + bS^2)/ab]\rho_y,$$

$$\Delta_y\phi_x = \phi_x(x,y+1) - \phi_x(x,y) = [-cs(a-b)/ab]\rho_x,$$

$$\Delta_x\phi_x = \phi_x(x+1,y) - \phi_x(x,y) = [(as^2 + bc^2)/ab]\rho_y, \text{ and}$$

$$\Delta_x\phi_y = \phi_y(x+1,y) - \phi_y(x,y) = [-cs(a-b)/ab]\rho_y,$$

where $c = \cos(\theta)$, $s = \sin(\theta)$, $\Delta_y\phi_y$ is the vertical difference in vertical phase $\phi_y$, $\Delta_y\phi_x$ is the vertical difference in horizontal phase $\phi_x$, $\Delta_x\phi x$ is the horizontal difference in horizontal phase $\phi_x$, and $\Delta_x\phi_y$ is the horizontal difference in vertical phase $\phi_y$. These equations reduce to the following:

$$S = \Delta_y\varphi_y/\rho_y + \Delta_x\varphi_x/\rho_x = 1/a + 1/b;$$

$$C = \Delta_x\varphi_x\rho_x - \Delta_y\varphi_y/\rho_y = [1/a - 1/b]\cos(2\theta);$$

$$D = -[4(\Delta_x\varphi_y/\rho_y)(\Delta_y\varphi_x/\rho_x) + C^2]^{1/2} = 1/a - 1/b;$$

$$a = 2/(S+D); b = 2/(S-D); \text{ and}$$

$$\theta = 0.5\arctan[(\Delta_y, \varphi_x/\rho_x + \Delta_x\varphi_y/\rho_y)/C].$$

Optical characteristics such as focal length, optical power and standardized apparent magnification may then be determined for each pixel using the maximum and minimum instantaneous apparent magnifications a and b, and the above equations.

Vertical disparity may also be evaluated for the windshield 12. Vertical disparity, experienced by an observer looking at an object at infinity, is the difference in altitude angle between the direction to the image of the object as seen from the left eye of the observer, and the direction to the image of the object as seen from the right eye. In order to calculate vertical disparity, the wrapped vertical phase distribution must be unwrapped using one of several known algorithms to obtain the unwrapped vertical phase $\phi_y$ at each pixel. Next, the vertical disparity $\Psi_e$ is determined for each pixel (x,y) using the following equation:

$$\Psi e(x,y) = \arctan([\rho(\phi_y(x,y) - \phi_y(x+x_e,y))/2\pi]/d_o,$$

where $d_o$ is the distance from the windshield 12 to the screen 22, $x_e$ is the horizontal distance corresponding to the interocular spacing (approximately 65 to 70 millimeters) projected to the windshield 12, and p is the pitch of the particular gray-scale pattern. It should be noted that vertical disparity evaluations are most useful for reflective products that produce relatively accurate images, such as flat mirrors.

Next, the optical characteristics for each point on the windshield 12 may be evaluated to determine whether the optical quality of the windshield 12 is acceptable. For example, the optical characteristics for each point may be compared with predetermined, acceptable values. As another example, the computer 20 may generate one or more output images or profiles that graphically represent optical characteristics of the windshield 12. Furthermore, such images or profiles may be color coded so that potential problem areas of the windshield 12 may be easily identified.

Advantageously, by utilizing gray-scale patterns rather than black and white patterns known as binary patterns, the method and apparatus enable optical characteristics to be determined at all points on the windshield 12. Consequently, the apparatus and method of the invention provide a significantly more complete determination of optical quality of the windshield 12 compared with prior art apparatuses and methods. Because the optical characteristics of the windshield 12 are determined by the computer 20, the invention also provides an efficient and accurate determination of optical quality of the windshield 12. Furthermore, because the method preferably includes determining standardized apparent magnification, optical performance of the windshield 12 in use conditions may be effectively predicted.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A method of determining reflective optical quality of a reflective product, the method comprising:

reflecting a first periodic gray-scale pattern off the product;

obtaining a first image of the first pattern with an image pickup device after the first pattern has reflected off the product; and determining optical quality of the product based on data obtained from the first image.

2. The method of claim 1 wherein reflecting a first periodic gray-scale pattern comprises reflecting a first sinusoidal grating off the product.

3. The method of claim 1 wherein reflecting a first periodic gray-scale pattern comprises reflecting a first sawtooth grating off the product.

4. The method of claim 1 further comprising:

reflecting a second periodic gray-scale pattern off the product, wherein the second pattern is phase-shifted with respect to the first pattern; and obtaining a second image of the second pattern with an image pickup device after the second pattern has reflected off the product;

wherein determining optical quality of the product further includes determining optical quality of the product based on the second image.

5. The method of claim 1 further comprising determining a phase for each of a plurality of pixels of the first image, wherein each pixel corresponds to a particular point on the product, and wherein determining optical quality of the product comprises determining optical quality of the product at each of a plurality of points on the product based on the phase at the corresponding pixel.

6. The method of claim 1 wherein determining optical quality of the product comprises determining apparent magnification for each of a plurality of points on the product.

7. The method of claim 1 wherein determining optical quality of the product comprises determining focal length for each of a plurality of points on the product.

8. The method of claim 1 wherein determining optical quality of the product comprises determining optical power for each of a plurality of points on the product.

9. The method of claim 1 wherein determining optical quality of the product comprises determining standardized apparent magnification for each of a plurality of points on the product.

10. The method of claim 1 wherein determining optical quality of the product comprises determining maximum apparent magnification and minimum apparent magnification for each of a plurality of points on the product.

11. The method of claim 10 wherein determining optical quality of the product comprises determining cylinder angle for each of the plurality of points on the product.

12. The method of claim 1 wherein determining optical quality of the product comprises determining vertical disparity for each of a plurality of points on the product.

13. A method of determining reflective optical quality of a reflective product, the method comprising:
    projecting a sequence of phase-shifted sinusoidal gratings onto the product such that the gratings are reflected off of the product and onto a reference plane;
    obtaining an image of each of the gratings within the sequence as reflected off of the product;
    determining a phase for each of a plurality of pixels of the images, wherein each pixel corresponds to a particular point on the product; and
    determining optical quality of the product at each of a plurality of points on the product based on the phase at the corresponding pixel point.

14. A method of determining reflective optical quality of a reflective product, the method comprising:
    positioning the product relative to an image generating device and an image pickup device such that light passing between the image generating device and the image pickup device reflects off of the product;
    generating a sawtooth grating with the image generating device;
    obtaining a first image of the sawtooth grating with the image pickup device, wherein the first image is influenced by the product;
    generating a uniformly white target with the image generating device;
    obtaining a second image of the uniformly white target with the image pickup device, wherein the second image is influenced by the product;
    generating a uniformly dark target with the image generating device;
    obtaining a third image of the uniformly dark target with the image pickup device wherein the third image is influenced by the product; and
    determining optical characteristics of the product based on the images.

15. An apparatus for determining reflective optical quality of a reflective product having light reflection properties, the apparatus comprising:
    an image generating device for generating a gray-scale pattern;
    an image pickup device for obtaining an image of the gray-scale pattern after the pattern has reflected off of the product; and
    an image analyzing device in communication with the image pickup device, the image analyzing device including instructions for determining optical quality of the product based on the image.

16. The method of claim 13 wherein determining a phase for each of a plurality of pixels of the images includes determining the phase for each pixel of the images based on variations in light intensities at each pixel of the images.

* * * * *